United States Patent [19]

Taylor

[11] 4,405,307

[45] Sep. 20, 1983

[54] NEEDLE ASSEMBLY AND METHOD FOR FABRICATING SAME

[76] Inventor: Alan N. Taylor, 2131 Martindale, SW., Wyoming, Mich. 49509

[21] Appl. No.: 329,200

[22] Filed: Dec. 10, 1981

[51] Int. Cl.³ ............................................... A61M 5/00
[52] U.S. Cl. ..................................... 604/165; 604/240
[58] Field of Search ................ 128/221, 215, 348–350, 128/214.4, 214; 604/164, 165, 192, 240, 283

[56] References Cited

U.S. PATENT DOCUMENTS

| | | | |
|---|---|---|---|
| 2,996,105 | 8/1961 | Holderith | 156/423 |
| 2,998,050 | 8/1961 | Hamilton | 156/378 |
| 3,133,849 | 5/1964 | Zenick | 156/423 |
| 3,359,619 | 12/1967 | Walkden | 156/567 |
| 3,523,531 | 8/1970 | Burke | 128/221 |
| 3,756,235 | 9/1973 | Burke et al. | 128/221 |
| 3,782,381 | 1/1974 | Winnie | 128/214.4 |
| 4,137,117 | 1/1979 | Jones | 156/294 |
| 4,233,974 | 11/1980 | Desecki et al. | 128/221 |
| 4,240,423 | 1/1980 | Akhavi | 128/218.05 |
| 4,240,425 | 12/1980 | Akhavi | 128/221 |

Primary Examiner—Stephen C. Pellegrino
Attorney, Agent, or Firm—Thomas R. Vigil

[57] ABSTRACT

The method is used for fabricating a needle assembly (10) comprising an outer cannula (12), an inner stylet (32), an orienting hub (16) on the proximal end (18) of the cannula (12) and a mating locating cap (40) on the proximal end (38) of the stylet (32).

The method comprises the steps of: fixing a plug (36) of plastic material on the proximal end (38) of the stylet (32); inserting the distal end (33) of the stylet (32) into the proximal end (18) of the cannula (12) having a hub (16) with locating means (28) at the proximal end (18) of the cannula (12); aligning the distal end (33) of the stylet (32) longitudinally and rotationally with the distal end (13) of the cannula (12); placing a locating cap (40) having a throughbore (42) over the plastic plug (36) on the proximal end (38) of the stylet (32) inserted into the cannula (12) and aligned at the outer end thereof with the stylet (32); positioning locating means (44) on the cap (40) in mating relationship with the locating means (26) on the hub (16); and, inserting solvent into the outer end (43) of the bore (42) in the cap (40) to solvent bond the cap (40) to the plug (36) on the stylet (32) with the cap (40) and hub (18) and stylet (32) and cannula (12) in proper alignment with each other.

33 Claims, 3 Drawing Figures

NEEDLE ASSEMBLY AND METHOD FOR FABRICATING SAME

TECHNICAL FIELD

The present invention relates to a needle assembly comprising a cannula and stylet and a method for fabricating the needle assembly. More specifically, the invention relates to a method for fixing a cap to the proximal end of the stylet with the cap in mating engagement with a hub at the proximal end of the cannula and with the distal ends of the stylet and cannula in longitudinal and rotational alignment.

DESCRIPTION OF THE PRIOR ART

Heretofore various method and apparatus have been proposed for securing a needle or cannula within a plastic body by means of an appropriate adhesive. Examples of such methods and apparatus can be found in the following U.S. Patents.

| U.S. PAT. NO. | PATENTEE |
| --- | --- |
| 2,996,105 | Holderith |
| 2,998,050 | Hamilton et al. |
| 3,133,849 | Zenick |
| 3,359,619 | Walkden |
| 3,523,531 | Burke |
| 3,756,235 | Burke et al. |
| 4,240,423 | Akhavi |
| 4,240,425 | Akhavi |

The Holderith U.S. Pat. No. 2,996,105 discloses a machine for connecting hypodermic needles with mountings. This patent discloses a machine for heat bonding cannulae, such as hypodermic needles, to mounting members, such as hubs, in order to provide a needle assembly capable of being assembled in a hypodermic syringe.

The Hamilton et al. U.S. Pat. No. 2,998,050 discloses a machine for automatically assembling hypodermic needles and more particularly a machine for attaching plastic hubs by means of an adhesive, such as epoxypolyamide to metal needle cannulas.

The Zenick U.S. Pat. No. 3,133,849 discloses another machine for assembling needle, cannula and hub assemblies using an adhesive.

The Walkden U.S. Pat. No. 3,359,619 discloses an apparatus for assembling hypodermic needles in which an adhesive is used to bind the needle to a glass barrel.

The Burke U.S. Pat. No. 3,523,531 discloses a plastic needle hub formed in two parts, one of which comprises an inner hub member and the other of which comprises an outer hub member which are held together by complementary engaging means. Adhesive is utilized in this method to retain a cannula in position engaging the inner hub member and also serves to secure the inner and outer hub members together.

The Burke, et al. U.S. Pat. No. 3,756,235 discloses a hypodermic syringe barrel and needle structure. In this structure a molded plastic barrel is formed with an integral tubular extension. A cannula is received within the tubular extension where a bonding material, such as an epoxy resin bonding material, previously inserted in the tubular extension, bonds the cannula to the tubular extension. A separately molded plastic cap member is sonically welded to the extension to form a permanent part thereof.

The Akhavi U.S. Pat. No. 4,240,423 discloses a hypodermic needle having a cannula secured to a transparent polycarbonate hub by an epoxy type adhesive.

The Akhavi U.S. Pat. No. 4,240,425 discloses a syringe with a plug type needle hub lock that includes a hub post to which a cannula is secured by an epoxy.

The needle assembly of the present invention is of the type that includes a cannula, a hub fixed to the proximal end of the cannula, a stylet and a cap fixed to the proximal end of the stylet. The hub has an adapter configured to mate with a syringe or other apparatus. The hub also has an orienting and locating notch. The cap is configured to be received on the adapter at the outer end of the hub and has a locating and orienting protrusion adapted to mate with the notch in the hub.

In fabricating a needle assembly with these components, it is necessary that the distal end of the cannula be aligned with the distal end of the stylet. In this respect, the distal end of the cannula often has a beveled point and the stylet has a mating beveled point so that the alignment requires both a rotational and longitudinal alignment of the beveled points of the stylet and cannula.

Also, the cap must be fixed to the proximal end of the stylet so that when it is received over the hub, the protrusion mates with the notch at the same time the beveled points align with each other.

Such a needle assembly is presently fabricated in several ways. One way is to grind and clean the beveled point of the stylet prior to fabricating the needle assembly and to grind and clean the beveled point of the cannula prior to fabricating the assembly. Then the hub is fixed to the proximal end of the cannula such as with an epoxy type adhesive. Then, the assembly of the hub on the proximal end of the cannula with epoxy therebetween is allowed to set while the epoxy cures and solidifies. Next, the stylet is inserted into the cannula until the beveled point thereof is aligned rotationally and longitudinally with the beveled point of the cannula. Then epoxy is placed on the proximal end of the stylet or within the bore in the cap, and the cap is placed over the proximal end of the stylet with the protrusion in mating engagement with the notch and, of course, with the beveled points in rotational and longitudinal alignment. The assembly of the stylet, cap and epoxy therebetween then is allowed to set until the epoxy cures and solidifies.

It will be appreciated that epoxy adhesives require a great deal of time to cure and usually a two part mixture is required and this requires expensive and elaborate mixing and dispensing equipment for mass production of needle assemblies. Accordingly, the cost of manufacture of the needle assembly of the type described above using a combination of plastic molding techniques and manual labor is quite expensive and costly.

An alternative way of fabricating such a needle assembly is first to affix, such as by means of an epoxy adhesive, the hub to the proximal end of the stylet. Then the stylet is inserted into the cannula until the cap is received over the hub with the locating protrusion and notch in mating engagement. Next, the distal ends of the stylet and cannula are both ground at the same time to form the two beveled points as a matched pair. This assembly must then be cleaned by disassembling the matched pair, flushing the cannula, cleaning the stylet and cannula (generally requiring several operations), all while keeping the cannula and stylet identified so as to assure the stylet is reassembled in the appropriate cannula with which it was ground, all of which is very elaborate and time consuming.

As will be described in greater detail hereinafter, the present invention provides a method for fabricating a needle assembly of this type in a simple and quick manner eliminating costly manual labor of grinding and cleaning the stylet and cannular points and/or the labor involved in preparing a two part mixture of epoxy and the curing time required. This saving in time, labor and equipment is accomplished by first fixing a plug of solvent bondable material to the proximal end of a previously ground stylet and then after proper alignment of the point of the stylet with the point of the cannula, fixing the cap to the plug using a solvent bonding technique which is accomplished in a few seconds.

Solvent bonding techniques, of course, are well known. See for example, the Jones U.S. Pat. No. 4,137,117. However, such techniques has not heretofore been utilized in the fabrication of a needle assembly of the type described above.

DISCLOSURE OF INVENTION

The needle assembly and method of fabricating same of the present invention differ from the assemblies and fabricating methods disclosed in the patents referred to above by providing a simple and quick means for forming a needle assembly comprising a stylet and a cannula. The stylet is received in the cannula with the distal ends thereof in rotational and longitudinal alignment and with a cap fixed on the proximal end of the stylet and in mating engagement with a hub fixed on the proximal end of the cannula.

According to the teachings of the present invention there is provided a method for fabricating a needle assembly comprising an outer cannula, an inner stylet, an orienting hub on the proximal end of the cannula and a mating locating cap on the proximal end of the stylet, said method comprising the steps of: fixing a plug of plastic material on the proximal end of the stylet; inserting the distal end of the stylet into the proximal end of the cannula having a hub with locating means at the proximal end of the cannula; aligning the distal end of the stylet longitudinally and rotationally with the distal end of the cannula; placing a locating cap having a throughbore over the plastic plug on the proximal end of the stylet inserted into the cannula and aligned at the outer end thereof with the stylet; positioning locating means on the cap in mating relationship with the locating means on the hub; and fixing the cap to the plug on the stylet with the cap and hub, and stylet and cannula in proper alignment with each other.

Also according to the invention there is provided a needle assembly comprising: a cannula, an orienting hub fixed to the proximal end of said cannula, said hub having locating means thereon, a stylet, a plug fixed to the proximal end of said stylet, and a cap received over said plug, and means for fixing said cap to said plug, said cap having locating means thereon adapted to mate with the locating means on said hub, and said cap having been fixed to said plug with said locating means of said hub and cap in mating engagement and with the distal end of said cannula in longitudinal and rotational alignment with the distal end of said stylet. The fixing of the cap to the plug in the method described above is preferably accomplished by inserting solvent into the outer end of a bore in the cap to solvent bond the cap to the plug; and the means for fixing said cap to said plug are preferably by solvent bonding the cap to said plug.

BEST MODE FOR CARRYING OUT THE INVENTION

Figure 1:
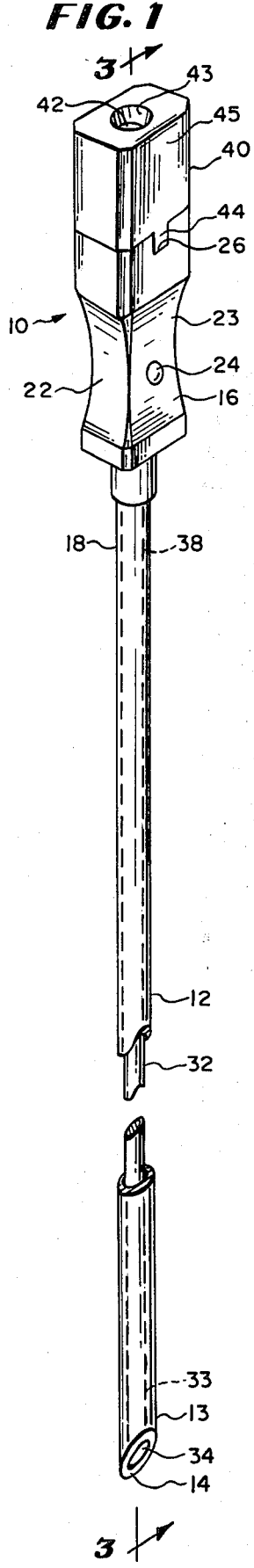
FIG. 1 is a perspective elevational view of the needle assembly of the present invention.

Referring now to the Figures, and particularly to FIG. 1, there is illustrated therein a cannula and needle assembly 10 constructed in accordance with the teachings of the present invention. This assembly 10 includes a cannula 12 having a distal end 13 ground to a beveled point 14. It is to be understood, however, that the assembly 10 can have a flat cylindrical end as opposed to a ground beveled point 14. A hub 16 is fixed to the proximal end 18 of the cannula 12 as shown. The cannula 12 can be made of a metallic or non-metallic material and is typically made of stainless steel. The hub 16 is typically made of a plastic material such as polyethylene or polypropylene and is fixed to the distal end 18 of the cannula 12 by insert molding or by an adhesive bonding epoxy.

Figure 2:
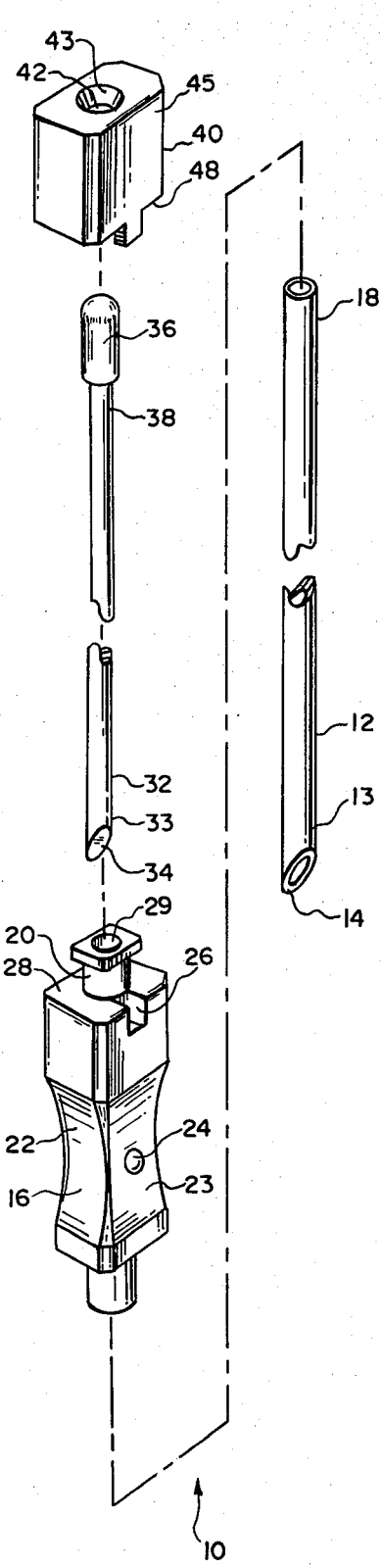
FIG. 2 is an exploded perspective view of the needle assembly of the present invention including a cap, a stylet with a plug fixed on the proximal end thereof, a hub and a cannula.

As best shown in FIG. 2, the hub 16 has an adapter 20 at the outer end thereof to facilitate attachment of the cannula 12 to a syringe or other apparatus.

The hub 16 also has curved sides 22 to facilitate gripping of the hub by the thumb and forefinger for inserting the needle assembly into a patient.

The needle assembly 10 is often referred to as a spinal needle since needle assemblies of this type are commonly used in performing a spinal tap.

The hub 16 further has, on one side 23 thereof, a locating knob or bump 24 which is aligned with the beveled side of the beveled point 14. Typically, a user of the needle assembly will grip the hub 22 between the thumb and forefinger with the knob or bump 24 facing upwardly and then insert the needle assembly 10 into the patient with the beveled side of the point 14 facing upwardly.

Still further, the hub 16 has a notch 26 extending inwardly from an end surface 28 from which the adapter 20 extends and inwardly from the side 23 of the hub 16. This notch 26 forms part of a locating and orienting means.

Figure 3:
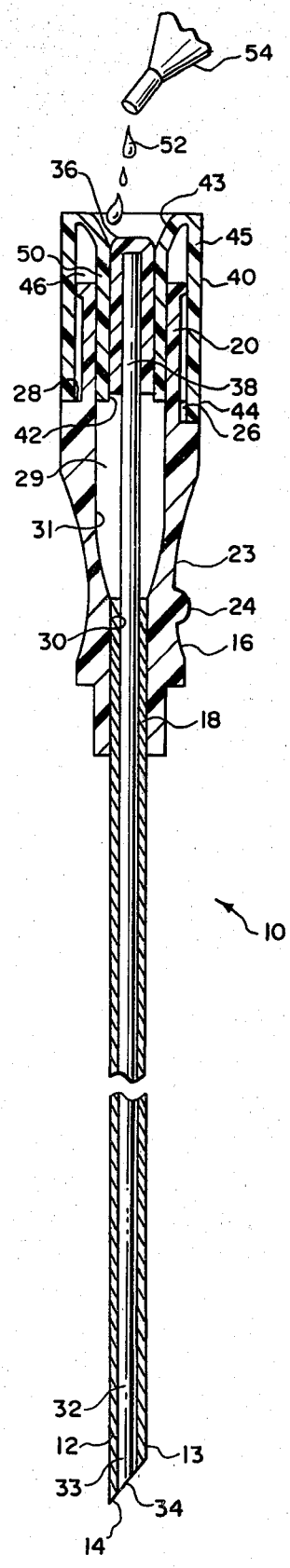
FIG. 3 is a sectional view of the needle assembly shown in FIG. 1, is taken along line 3—3 of FIG. 1 and shows the stylet aligned with the cannula and the cap received over the plug and in mating engagement with the hub as solvent is dropped into the cap for solvent bonding the cap to the plug.

As best shown in FIG. 3, the hub 16 has a throughbore 29 extending therebrough. The lower or inner portion 30 of the throughbore is of a diameter sufficient to receive the proximal end 18 of the cannula 12 which is fixed therein by inserting molding or by an adhesive bonding epoxy whereas the upper or outer portion 31 is of a larger diameter so as to form the throughbore 30 with a countersunk portion 31. This larger diameter portion 31 of the throughbore extends to and opens onto the adapter 20 for coupling to a syringe.

The needle assembly 10 further includes a wire, e.g., stainless steel, stylet 32 having a distal end 33 ground to a beveled point 34 as shown in FIG. 2.

According to the teachings of the present invention, a plug 36 of solvent bondable material such as ABS is fixed, such as by insert molding or by use of an adhesive bonding epoxy, to the proximal end 38 of the stylet 32. The plug 36 has a length, e.g., ¼ inch, to provide a bonding surface on the plug 36 of sufficient length for facilitating the fabrication of the needle assembly 10 as described above.

A cap 40, also made of solvent bondable material such as ABS, is fixed to the plug 36 and is provided with a throughbore 42 (FIG. 3) larger than the plug 36 and of sufficient length to accommodate different lengths of cannulas 12 and stylets 32 as will be encountered with extremes of tolerances of the cannula 12 and stylet 32. For example, the length is sufficient to accommodate a long cannula 12 and short stylet 32 or a short stylet 32 and long cannula 12. A typical length of the bore 42 is ⅜ inch.

Also, the bore 42 is flared or conical at the outer end thereof at 43.

The cap 40 is placed over the plug 36 and fixed thereto in a quick and simple manner using the method of the present invention as will be described in greater detail below.

The cap 40 is fixed to the plug 36 in an aligned manner so that when the stylet 32 with the cap 40 fixed to the proximal end 38 thereof is inserted into the cannula 12, a protrusion 44 extending downwardly from one side 45 of the cap 40 will be received in the notch 26. This projection or protrusion 42 will also be aligned with the upwardly facing bevel of the beveled point of the stylet 32.

Also, when the cap 40 is fitted over the adapter 20 and flush adjacent the end face 28 with the protrusion 42 received in the notch 26 as shown in FIG. 1, the beveled point 34 of the stylet 32 is in rotational and longitudinal alignment with the beveled point 14 of the cannula 12 as shown in FIG. 1.

As shown in FIG. 3, a channel or generally annular (but squared) slot 46 is formed in the cap 40 extending into the cap 40 from a bottom edge 48 thereof about an inner hub 50 having the throughbore 42 extending therethrough. The channel or slot 46 receives and accommodates the adapter 20.

In accordance with the teachings of the present invention, the needle assembly 10 is fabricated first by fixing the hub 16 on the proximal end 18 of the cannula 12 such as by insert molding or by use of an adhesive bonding epoxy.

This is done after the beveled point 14 has been ground and cleaned on the distal end 13 of the cannula 12 and is molded or adhered on the proximal end 18 so that the locating bump 24 is in alignment with the bevel face of the beveled point 14.

The stylet 32 is first ground at the distal end 33 thereof to form the beveled point 34 with the same angle or bevel of inclination as the bevel point 14 of the cannula 12. Then a plug of solvent bondable material 36 is fixed to the proximal end 38 of the stylet 32 such as by insert molding or by use of an adhesive bonding epoxy.

It will be appreciated, of course, that the length of the stylet 38 is chosen to be a little bit greater than the length of the cannula 12 and hub 16 mounted thereon.

These steps in the fabrication of the assembly, namely the grinding of the beveled point 14 on the cannula 12 and the affixing of the hub 16 on the proximal end 18 thereof, as well as the grinding of the beveled point 34 on the stylet 32 and the affixing of the plug 36 on the proximal end 38 thereof are performed using conventional (mass) production techniques. Also, since the length of the cannula 12 within a certain tolerance and the length of the stylet within a certain tolerance have already been predetermined, no special alignment is required by manual labor.

Then, in the completion of the fabricating of the needle assembly 10, an assembler, with the aid of a fixture, inserts the beveled point 34 of the stylet 32 through the larger diameter bore portion 31 in the hub 16 and into the proximal end 18 of the cannula 12 and pushes the stylet 32 into the cannula 12 until the beveled point 34 is at the distal end 13 of the cannula 12. Here the fixture rotationally and longitudinally aligns the beveled point 34 with the beveled point 14. Next, the assembler places the cap 40 over the plug 36 with the protrusion 42 received in the notch 26.

At this point, the assembler will hold the assembly in a generally upright or tilted position and drop a few drops of solvent from a dispenser 54 into the conical end 43 of the bore 42 in the cap 40. This solvent, which can be methyl ethyl ketone, will then flow about the plug 36 and between the outer surface of the plug 36 and bore 42 at least in the area adjacent the conical end 43 dissolving mating surfaces and then fusing them (as the solvent dries) to fix the plug 36 to the cap 40. This solvent bonding takes place in a few seconds such that after applying a few drops of solvent and holding the assembly momentarily, the assembler can then place a protective plastic tube over the cannula 12 to protect the cannula 12 and the beveled points 14 and 34 of the needle assembly 10 and then place the assembly 10 on a conveyor belt or in a receptacle for finished assemblies which are now ready for packaging.

By molding the plug 36 on the proximal end 38 of the stylet 32 and by using a solvent bonding technique for fixing the cap 40 to the plug 36 once the stylet has been properly aligned with the cannula 12, the method of the present invention saves much time, manipulation, and equipment that otherwise would be required in using an adhesive epoxy resin composition for fixing the cap 40 to the proximal end 38 of the stylet 32. As a result, a plastic molding company using the method of the present invention can manufacture, assemble and sell the needle assemblies 10 economically and at a price competitive with mass produced needle assemblies which are manufactured by using complex and expensive machinery.

From the foregoing description, it will be apparent that the method for fabricating a needle assembly and the needle assembly 10 formed thereby as described above have a number of advantages, some of which have been described above and others of which are inherent in the invention. Specifically, the method of the present invention enables a plastic molding company to simply, quickly and inexpensively fabricate needle assemblies of the type which include a cannula and stylet with mating hub and cap.

Also it will be apparent from the foregoing description that modifications can be made to the method of fabricating a needle assembly and the needle assembly 10 formed thereby without departing from the teachings of the present invention. Accordingly, the scope of the invention is only to be limited as necessitated by the accompanying claims.

I claim:

1. A method for fabricating a needle assembly comprising an outer cannula, an inner stylet, an orienting hub on the proximal end of the cannula and a mating locating cap on the proximal end of the stylet, said method comprising the steps of: fixing a plug of plastic material on the proximal end of the stylet; inserting the distal end of the stylet into the proximal end of the cannula having a hub with locating means at the proximal end of the cannula; aligning the distal end of the stylet longitudinally and rotationally with the distal end of the cannula; placing a locating cap having a throughbore over the plastic plug on the proximal end of the stylet inserted into the cannula and aligned at the outer end thereof with the stylet; positioning locating means on the cap in mating relationship with the locating means on the hub; and inserting solvent into the outer end of the bore in the cap to solvent bond the cap to the plug on the stylet with the cap and hub, and stylet and cannula in proper alignment with each other.

2. The method according to claim 1 wherein said hub is made of a material from the group consisting of polyethylene and polypropylene.

3. A needle assembly made by the method of claim 1.

4. The method according to claim 1 wherein said plug is made of solvent bondable material.

5. The method according to claim 4 wherein said solvent bondable material is ABS.

6. The method according to claim 1 wherein said cap is made of solvent bondable material.

7. The method according to claim 6 wherein said solvent bondable material is ABS.

8. The method according to claim 1 wherein said plug is fixed to said stylet by inserting molding said plug to the stylet.

9. The method according to claim 1 wherein said plug is fixed to said stylet by an adhesive.

10. The method according to claim 9 wherein said adhesive is an epoxy.

11. The method according to claim 1 wherein said locating means on the cannula hub is a notch formed therein.

12. The method according to claim 1 wherein said locating means on said stylet cap is a protrusion designed to be matingly received in the notch in the cannula hub.

13. The method according to claim 1 wherein said solvent comprises methyl ethyl ketone.

14. A needle assembly made by the method of claim 13.

15. The method according to claim 1 wherein the points on the distal ends of the cannula and the stylet are ground and cleaned separately prior to formation of the assembly.

16. A needle assembly made by the method of claim 15.

17. The method according to claim 1 wherein the solvent is quick acting and bonds the cap to the plug in a few seconds.

18. A needle assembly comprising: a cannula, an orienting hub fixed to the proximal end of said cannula, said hub having locating means thereon, a stylet, a plug fixed to the proximal end of said stylet, and a cap received over said plug, and means for fixing said cap to said plug, said cap having locating means thereon adapted to mate with the locating means on said hub, and said cap having been fixed to said plug with said locating means of said hub and cap in mating engagement and with the distal end of said cannula in longitudinal and rotational alignment with the distal end of said stylet.

19. The assembly according to claim 18 wherein said hub is made of a material selected from the group consisting of polyethylene and polypropylene.

20. The assembly according to claim 18 wherein said cap is fixed to said plug by a solvent.

21. The assembly according to claim 20 wherein said solvent comprises methyl ethyl ketone.

22. The assembly according to claim 20 wherein said solvent is a quick acting solvent which bonds said cap to said plug in a few seconds.

23. The assembly according to claim 18 wherein said plug is made of a solvent bondable material.

24. The assembly according to claim 23 wherein said solvent bondable material is ABS.

25. The assembly according to claim 18 wherein said cap is made of solvent bondable material.

26. The assembly according to claim 26 wherein said solvent bondable material is ABS.

27. The assembly according to claim 18 wherein said plug is fixed to said stylet by insert molding said plug to said stylet.

28. The assembly according to claim 18 wherein said plug is fixed to said stylet by an adhesive.

29. The assembly according to claim 28 wherein said adhesive is an epoxy.

30. The assembly according to claim 18 wherein said locating means on the cannula hub is a notch formed therein.

31. The assembly according to claim 30 wherein said locating means on said stylet cap is a protrusion on said cap configured to be matingly received in said notch in said hub.

32. The assembly according to claim 18 wherein said points of said cannula and said stylet are ground and cleaned separately prior to formation of the assembly.

33. A method for fabricating a needle assembly comprising an outer cannula, an inner stylet, an orienting hub on the proximal end of the cannula, and a mating locating cap on the proximal end of the stylet, said method comprising the steps of: fixing a plug of plastic material on the proximal end of the stylet; inserting the distal end of the stylet into the proximal end of the cannula having a hub with locating means at the proximal end of the cannula; aligning the distal end of the stylet longitudinally and rotationally with the distal end of the cannula; placing a locating cap having a throughbore over the plastic plug on the proximal end of the stylet inserted into the cannula and aligned at the outer end thereof with the stylet; positioning locating means on the cap in mating relationship with the locating means on the hub; and fixing the cap to the plug on the stylet with the cap, hub, stylet, and cannula in proper alignment with each other.

* * * * *